United States Patent [19]
Avallone et al.

[11] Patent Number: 5,320,967
[45] Date of Patent: Jun. 14, 1994

[54] BOILER SYSTEM LEAK DETECTION

[75] Inventors: Stanley C. Avallone, Lockport; Roger W. Fowee, Wheaton; James R. MacDonald, Chicago; Nicholas J. Furibondo, Naperville, all of Ill.

[73] Assignee: Nalco Chemical Company, Naperville, Ill.

[21] Appl. No.: 53,861

[22] Filed: Apr. 20, 1993

[51] Int. Cl.$^5$ .................. G01N 35/02; F22B 37/42
[52] U.S. Cl. .................... 436/50; 122/504; 436/55; 436/172; 252/408.1; 252/964; 165/70
[58] Field of Search .................. 436/50, 55, 172; 252/408.1, 964; 122/504; 165/11.1, 70

[56] References Cited

U.S. PATENT DOCUMENTS

| | | | |
|---|---|---|---|
| 4,368,694 | 1/1983 | Ward et al. | 122/504 |
| 4,724,799 | 2/1988 | Traiteur et al. | 122/504 |
| 4,783,314 | 11/1988 | Hoots et al. | 422/3 |
| 4,966,711 | 10/1990 | Hoots et al. | 210/697 |
| 4,992,380 | 2/1991 | Moriarty et al. | 436/55 |
| 5,006,311 | 4/1991 | Hoots et al. | 422/62 |
| 5,041,386 | 8/1991 | Pierce et al. | 436/50 |
| 5,128,419 | 7/1992 | Fong et al. | 525/351 |

FOREIGN PATENT DOCUMENTS

| | | |
|---|---|---|
| 0062306 | 10/1982 | European Pat. Off. |
| 2657851 | 6/1978 | Fed. Rep. of Germany |
| 2238383 | 5/1991 | United Kingdom |

OTHER PUBLICATIONS

"Practical Applications of Tracers—Beyond Product Monitoring", J. E. Hoots, Cooling Tower. Institute 1990 Annual Meeting, Technical paper No. TP90-01, 14 pages, presented Feb. 1990.

"Effluent Monitoring For Oil in Water", K. Coursin, Pollution Engineering, pp. 100-102 Nov., 1988.

"Use of Fluorescence Spectroscopy for Monitoring Petroleum Hydrocarbon Contamination in Estuarine and Ocean Waters", W. A. Maher, Bull. Environ. Contam. Toxicol, 30, pp. 413-419, 1983.

"Fluorescence Cell Design and Use to Determine Crude Oil in Water", P. John, E. R. McQuat and I. Soutar, Analyst (London), vol. 107, pp. 221-223, Feb., 1992.

"Spectroscopic Techniques for Quality Assurance of Oil Field Corrosion Inhibitors", J. A. Martin and F. W. Valone, National Association of Corrosion Engineers, Aug., 1985, vol. 41, No. 8, pp. 465-473, presented Corrosion 84, Paper No. 233, Apr., 1984, New Orleans, Louisiana.

(List continued on next page.)

Primary Examiner—Henry C. Yuen
Attorney, Agent, or Firm—Joan I. Norek; Robert A. Miller; Joseph B. Barrett

[57] ABSTRACT

Leakage of water from a boiler water system wherein steam is generated in a boiler from feedwater fed to the boiler, and the concentration of impurities in the boiler water within the boiler is reduced by withdrawing fractions thereof as blowdown while admitting additional feedwater as boiler-water makeup, is determined. The boiler has a concentration cycle value, the concentration cycle value being the average value of the concentration of an inert component in the blowdown at steady state ($C_F$) divided by the concentration of the inert component in the feedwater ($C_I$). The concentration of the inert component in the boiler at steady state varies from a high concentration $C_H$, having a value that is higher than $C_F$, to a low concentration $C_L$, having a value between the ($C_I$) and the ($C_F$), within a time period. The method comprises:
  employing as the inert component an inert tracer;
  sensing a characteristic of the inert tracer in the boiler at steady state equivalent to its concentration in the boiler water;
  converting the sensed characteristic to a value equivalent to the concentration of the inert tracer in the boiler water; and
  activation of a signal when a variance in the cyclic concentration fluctuation of said inert tracer occurs that is consistent with a leakage of boiler water.

22 Claims, 4 Drawing Sheets

OTHER PUBLICATIONS

"The Existence of Imidazoline Corrosion Inhibitors", J. A. Martin and F. W. Valone, National Association of Corrosion Engineers, May, 1985, vol. 41, No. 5, pp. 281-287 presented Corrosion 84, Paper No. 232, Apr. 1984, New Orleans, Louisiana.

Literature Search Report No. 4118, Apr. 13, 1992, subject entitled "Use of Natural Fluorescence to Detect Process Leaks Into Water Systems, Expecially Cooling Towers", pp. 1-24.

Literature Search report No. 3244, Jul. 19, 1990, subject entitled "Continuous On-line Fluorescence Monitoring of Soluble Oils in Water, Wastewater or Other Aqueous Solutions" pp. 1-26 plus 7 additional pages.

"Use of Fluorescent Tracers to Monitor Internal Boiler Treatments and to Determine Boiler Operating Parameters", R. W. Fowee and C. C. Pierce, Nalco Chemical Company, p. 10, Presented at the National Association of Corrosion Engineers Corrosion Meeting, Las Vegas, Nevada, Apr. 23-27, 1990.

Literature Search Report No. 4294, Sep. 29, 1992, subject entitled "Patent Extension of Trasar Technology: Uses of Tracers", pp. 1-64.

BOILER SYSTEM LEAK DETECTION

TECHNICAL FIELD OF THE INVENTION

The present invention is in the technical field of boiler maintenance, and in particular the detection of leakage in a boiler system.

BACKGROUND OF THE INVENTION

A boiler is a vessel in which water is vaporized into steam by the application of heat, typically on a continuous basis. The steam generated is most often used either as a direct or indirect heat transfer medium and/or to generate electric power. High pressure and/or high capacity boilers generally are water-tube boilers in which water is circulated within tubes and the applied heat (combustion products such as flame and hot combustion gases) flows across the outside of the tubes. Some of these water tubes may comprise the walls of the furnace in which the heat-generating combustion occurs.

Most water tubes are in the boiler furnace and therefore leakage in a boiler system can be a very grave matter. For instance, the serious risk of smelt/water explosions caused by leakage in recovery boilers is well recognized in the pulp and paper industry, and industry-wide efforts seeking ways to reduce the risk are ongoing. Such goal is of significant interest to recovery boiler manufacturers, insurers and pulp mills which operate recovery boilers which burn organic liquors having high caustic levels. Explosions caused by leakage is not a concern for power boilers which burn oil or natural gas, because leaking water will just flash to steam, but nonetheless leakage decreases boiler operation efficiency and increases boiler maintenance costs, and thus leak detection is desirable. A primary leakage concern for boilers in the chemical process industry is contamination of process streams, for instance in ammonia production plants having an ammonia stream on one side of the boiler wall. The nuclear power generation industry has a serious need to avoid boiler-water leakage because fluids with a high radioactive contamination level are under high pressure and a leakage could spread such contamination outside of the initial containment.

Many technologies have been and are currently being developed for detecting boiler water leaks, particularly furnace-water-wall leaks, at the earliest possible moment. These technologies include the use of steam drum level control, computer algorithm, and others. Among the recently developed technologies for early leak detection is the use of sodium ion concentration to detect tube leaks (balancing the sodium ion mass between the boiler feedwater and blowdown), but the sensitivity of the sodium-specific electrode is affected by pH among other feedwater variables. Some boiler operators are currently using complex computer systems in attempts to use boiler operating data for leakage detection with intricate calculations.

A leak detection method of greater sensitivity is needed, because the early detection of leaks requires detection of an extremely small water loss from a dynamic water system. A leak detection method of great sensitivity must be independent of chemical species that might be present in boiler feedwater in amounts varying with the operation efficiency of the demineralizer, mixed bed polisher or other techniques used to purify the feedwater prior to introduction into the boiler.

It is an object of the present invention to provide a boiler-tube leak detection method of great sensitivity that is both cost efficient and relatively simple to operate. It is an object of the present invention to provide a method for the early detection of leaks which can detect an extremely small water loss from a dynamic boiler water system. It is an object of the present invention to provide a leak detection method of great sensitivity that is independent of quality variations in boiler feedwater, and thus is independent of the operational efficiency of the demineralizer, mixed bed polisher or other techniques used to purify the feedwater prior to introduction into the boiler. These and other objects of the present invention are described further below.

DISCLOSURE OF THE INVENTION

The present invention provides a method of determining leakage from a boiler water system wherein steam is generated from the feedwater fed to the boiler, and the concentration of impurities in the boiler water is reduced by withdrawing fractions thereof as blowdown while admitting additional feedwater as boiler-water makeup. Such a boiler has a concentration cycle value, which is the value of the average concentration ("$C_F$") of an inert component in the normal blowdown at steady state divided by its concentration ("$C_I$") in the feedwater. The concentration of the inert component in the boiler at steady state varies from a high concentration "$C_H$", having a value that is higher than $C_F$, to a low concentration "$C_L$", having a value between the ($C_I$) and the ($C_F$), within a time period A. This method is comprised of the following steps:

1. Employing as the inert component an inert tracer added to the feedwater in a known concentration ($C_I$);
2. Sensing a characteristic of the inert tracer in the boiler at steady state equivalent to its concentration in the boiler water;
3. Converting the sensed characteristic to a value equivalent to the concentration of the inert tracer in the boiler water;
4. Optionally recording the cyclic concentration fluctuation from $C_H$ to $C_L$ of the inert tracer in the boiler water; and
5. Activation of a signal when a variance in the cyclic concentration fluctuation of the inert tracer occurs that is consistent with, and thus indicative of, a leakage of boiler water.

The concentration of the inert tracer in the boiler at any point in time is determined from the concentration of the tracer in a sidestream that taps the boiler water, which preferably is a sidestream off the blowdown line and which preferably taps the boiler water on a continuous basis.

There are a plurality of indicators of the occurrence of a variance in the cyclic concentration fluctuation of the inert tracer consistent with a leakage of boiler water, and a given boiler may be monitored for one or more of such variance indicators.

In a preferred embodiment of the present invention, the variance indicator is an inert tracer concentration in the boiler that has a value less than that equivalent to the normal low $C_L$ concentration of the inert tracer, for instance an inert tracer concentration of $C_L - C_D$, preferably wherein $C_D$ is at least about 5 or 10 percent of $C_L$, and thus signal activation occurs when the tracer concentration in the boiler falls to 90 or 95 percent of its normal lowest concentration. Such a variance indicator is not time dependent and a condition consistent with water leakage from the boiler is indicated whenever such a variance indicator occurs.

In another preferred embodiment of the present invention, the variance indicator is an inert tracer concentration in the boiler that fails to reach the normal high $C_H$ concentration within a set time period, referred to herein as time period B. That time period B could be set at about twice that of the time it normally takes for the concentration of the inert tracer to reach the $C_H$ concentration from the $C_L$ concentration, which normal time frame is referred to herein as time period A, and is about one-half of a complete inert tracer concentration cycle. In a preferred embodiment such a variance indicator is monitored in a boiler with open/close blowdown valve operations, and the time period B is measured from the closing of the blowdown valve, shutting off the normal blowdown flow, to the time at which the blowdown valve would normally reopen. In such a boiler the time period B would be about equivalent in length to time period A.

In many large boilers the blowdown valve is normally open and the blowdown rate would not normally fall to zero. Instead the blowdown valve adjusts the blowdown rate depending upon some indicated impurity build-up within the boiler, which indication may be based on concentration readings of an inert tracer in the boiler as it fluctuates between $C_H$ and $C_L$. When the inert tracer concentration in the boiler has a value less than that equivalent to the normal low $C_L$ concentration of the inert tracer, for instance an inert tracer concentration of $C_L - C_D$, preferably wherein $C_D$ is at least about 5 or 10 percent $C_L$, the normally-open blowdown valve would close in response to such a reading. If the tracer monitoring apparatus is ahead of the blowdown valve, the analyzer would see a tracer concentration while a flow meter downstream of the blowdown valve would see no flow, and the combination of conditions would be consistent with a boiler leak. If instead the tracer monitoring apparatus is downstream of the blowdown valve, the analyzer would see no tracer concentration and that condition would be consistent with a boiler leak.

In another preferred embodiment the variance indicator in the normal fluctuation in the inert tracer concentration in the boiler between $C_H$ and $C_L$ would be compared to another operating parameter and the potential boiler water leakage signal would be activated only when an imbalance in such other operating parameter is also seen. The inert tracer variance indicator preferably would be either the detection of an inert tracer concentration value less than that equivalent to its normal low $C_L$ concentration of the inert tracer, for instance an inert tracer concentration of $C_L - C_D$, preferably wherein $C_D$ is at least about 5 or 10 percent $C_L$, or an inert tracer concentration in the boiler that fails to reach the normal high $C_H$ concentration within the set time period B. Such a variance indicator would be compared, for instance, to the balance in the steam load determined from flow signals. In this embodiment, an imbalance between the rate feedwater is flowing into the boiler and the rate steam is being discharged therefrom must be seen by the monitors at the same time a variance indicator in the normal fluctuation of the inert tracer concentration indicates a leak before a signal is activated. In another embodiment, the other operating parameter is the holding time index. If an imbalance is seen between the holding time index and the calculated blowdown rate at the same time a variance indicator in the normal fluctuation of the inert tracer concentration is detected, then the combined conditions indicate a leak and a signal is activated

PREFERRED EMBODIMENTS OF THE INVENTION

Figure 1:
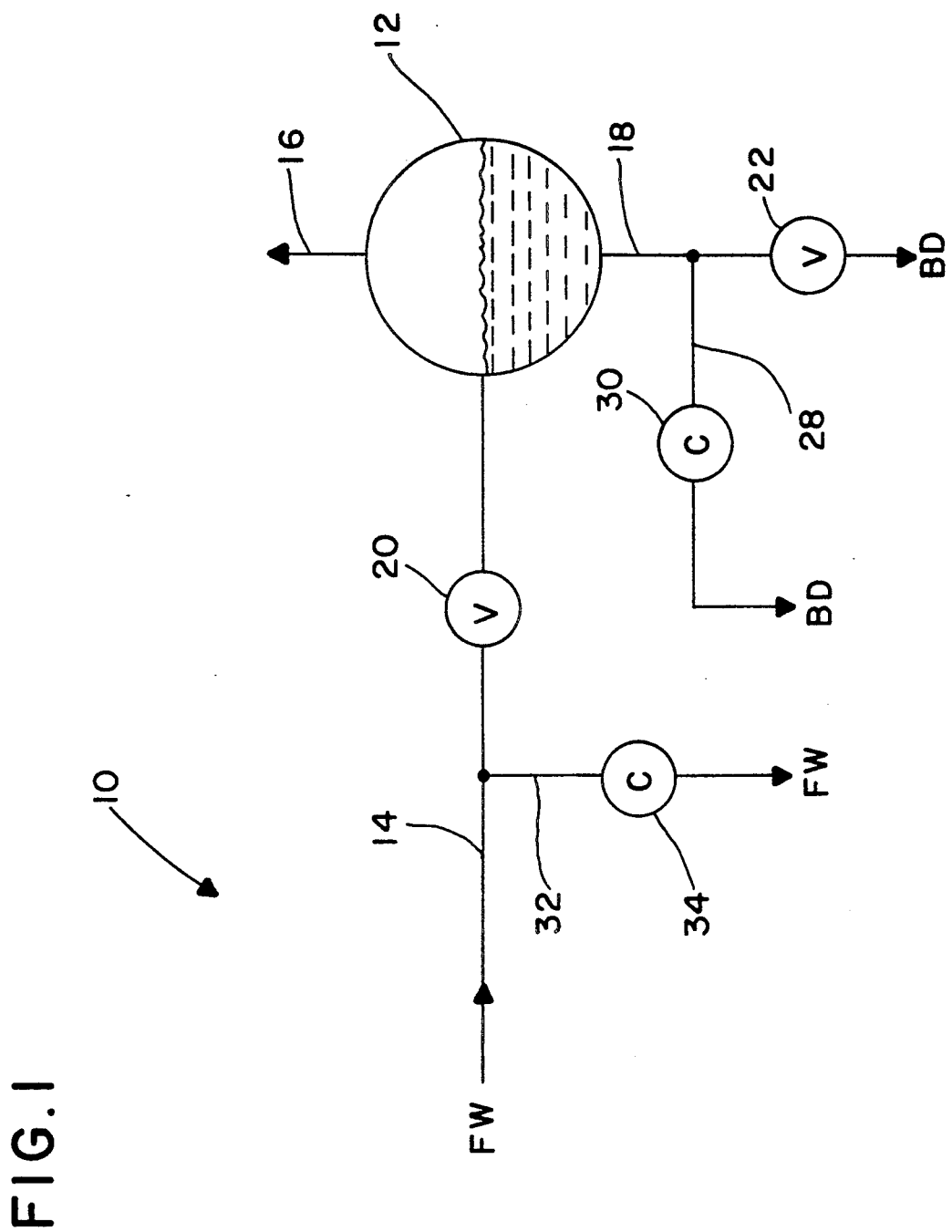
FIG. 1 is a boiler system comprised of a boiler, a feedwater line, a steam line, and a blowdown line shown in diagrammatical form.

A boiler cycles of concentration is an operating parameter that is either well monitored, or should be well monitored. Limits on boiler cycles of concentration, so as to limit the maximum impurity concentration within a boiler, are routinely set by boiler and turbine manufacturers, water treatment companies and the industrial plants employing the boilers. Such limitations are intended for, and are generally necessary to, the avoidance of serious scale formation/deposition despite an otherwise adequate water treatment program. Boiler feedwater, which normally is comprised of both makeup water and recirculated condensate water, contains some impurities regardless of the extent to which such waters are treated before being fed to a boiler. When steam is generated, substantially pure $H_2O$ vapor is discharged from the boiler, leaving the impurities (the dissolved and suspended solids) behind, which increases their concentration in the boiler water. The discharged steam is replaced by contaminant-containing feedwater. An ever increasing concentration of dissolved and suspended solids in the boiler water would inevitably result in very serious problems, including deposit formation, corrosion, foaming and carryover, decreased heat transfer efficiency, boiler tube failure or occlusion, and the like. Boiler-impurities concentration (boiler solids concentration) is offset by withdrawing water as normal blowdown. The heat energy in the normal blowdown, however, is a major factor reducing a boiler's thermal efficiency, and therefore a blowdown rate in excess of that required to limit solids concentration is preferably avoided. An excessive blowdown rate also unnecessarily increases water costs.

The ratio of solids concentration in the normal blowdown to the solids concentration in the feedwater is called the "cycle value", "cycles of concentration", "concentration cycles" or "cycles" of a boiler operation. If a boiler is being operated on too low of a concentration cycle, the blowdown rate is too high and the operation is unnecessarily inefficient. The excessive loss of heat with the excessive blowdown decreases thermal efficiency and water costs increase at the same time. If a boiler is being operated on too high of a concentration cycle, the blowdown rate is too low and the potential for solids-derived problems, such as scale deposit and corrosion, is great. Thus the cycles of concentration is preferably one of the primary operating parameters monitored.

The method of the present invention may include the monitoring of a boiler operation's cycles of concentration. U.S. Pat. No. 5,041,386, Claudia C. Pierce, Roger W. Fowee, and John E. Hoots, issued Aug. 20, 1991, incorporated hereinto by reference, discloses the use of inert tracers to monitor boiler concentration cycles. Boiler cycles are calculated by adding an inert tracer to the feedwater being charged to the boiler in a known concentration, and then determining an analog of its concentration in the normal blowdown. If the cycles value does not compare to the standard operating value, which may be the cycles value proposed by the boiler manufacturer or set by the operator or suggested by water-treatment supplier, then the blowdown rate and/or the dosage of water-treatment agent can be adjusted. The inert tracer preferably is employed to determine the cycles (impurity or contaminant concentration within the boiler water) on a continuous basis. The inert tracer may be used for other purposes, such as the determination of percent holding time (half-life time), as a reference standard in the monitoring of concentration of water-treatment agent concentration level, and the like, concomitantly with the cycles determination.

Boiler cycles (cycles value, concentration cycles, cycles of concentration and the like) as such terminology is used herein, as understood generally in the boiler field, is the ratio of the concentration of a particular impurity or component ("IMP") in the normal blowdown at steady state (final concentration or "$C_F$") to its concentration in the feedwater (initial concentration or "$C_I$"), which ratio is determined from the following Formula I:

Formula I
$$\text{cycles} = (C_F)/(C_I) \text{ or } \frac{\text{steady state normal blowdown concentration of } IMP}{\text{feedwater concentration of } IMP}$$

and the value, which is an equilibrium value, will always be greater than one since the impurity IMP in the normal blowdown is always more concentrated than in the feedwater due to water removed as steam. (Upsets in feedwater quality of a magnitude sufficient to lower the cycles value to less than one are not tolerable in the boiler field and would never occur outside of a major boiler operation failure.)

In the process of the present invention, the inert tracer is the "impurity" or "IMP" of Formula I above, and the acronym "IT" for "inert tracer" can be employed in substitution for the "IMP" designation. The present invention exploits the phenomenon that in any practical boiler system operation the $C_F$ is not an absolute constant and the cycles value assigned to a boiler operation is based on an average value of $C_F$, and thus the present invention goes farther than the determination of the cycles value and need not include a cycles value determination. Moreover, for purposes of the present invention the inert tracer is to be introduced into the boiler system in a known and uniform proportion to the feedwater, and it is preferably, but not necessarily, introduced into the boiler system as a component of the feedwater in a known and constant concentration with respect to the feedwater.

Intermediate and high pressure boilers have heat transfer rates in excess of 100,000 Btu/ft$^2$-hr (2,500 cal/m$^2$-hr) and the presence of an even extremely thin deposit layer within the boiler would cause a serious elevation in the temperature of the tube metal. Therefore the feedwater purity is very high and the permitted concentration of impurities introduced with the feedwater is very low. These are almost invariably high cycles value boilers with almost constant steam generation demands. When the cycles values of such boilers are monitored with the inert tracers disclosed in U.S. Pat. No. 5,041,386, which do not appreciably carry over into the steam, and which can be selectively detected at very low concentrations (for instance 0.005 ppm or less), it has been found that in a given boiler system not only can the average cycles value be determined from the average $C_F$, but the normal range of the $C_F$ fluctuation can also be determined and a variance therefrom detected. This can also be done for boilers that are not intermediate or high pressure boilers. (The only boiler operation parameters that may exclude the use of some of the preferred embodiments of present invention are pressures in excess of 1,800 psig, which pressures may lead to decomposition of the presently preferred sulfonated naphthalene and sulfonated pyrene inert tracers that are described below.)

The process of the present invention, as mentioned above, preferably activates a signal when such an excursion from the normal range of the $C_F$ fluctuation is detected. The variance indicators discussed above also represent a drop in the normal actual cycles value range (the actual cycles value fluctuates with the fluctuation of $C_F$), a drop in the normal average cycles value and a drop in the normal average $C_F$ after reaching a steady state. Such changes, without any accompanying change in the boiler steam load (these boilers are normally at constant mass flow rates) indicate a leak.

The process of the present invention in an embodiment preferably comprises a continuous monitoring of the concentration of an inert tracer in a boiler using an inert tracer introduced with the feedwater. The continuous determination of the inert tracer concentration in the boiler detects any variance indicator in its fluctuation of the inert tracer between the normal $C_H$ and $C_L$, and any drop below a setpoint, which setpoint is predetermined based on the normal fluctuation of the inert tracer between $C_H$ and $C_L$ of that boiler, activates a leak-alert signal. The boiler operator is thereby alerted to the significant potential that a leak is occurring, and can activate and/or focus on other system checks and/or inspections (for instance of the firebox and/or ashpit) to confirm and/or locate the leakage.

Steady state as such terminology is used herein, as understood generally in the boiler field, is the condition that exits when the concentration of the inert tracer (or other stable substance introduced into the boiler with the feedwater) in the water of the boiler system reaches a uniform, repetitious cycling fluctuation of the inert tracer from a predictable high concentration ($C_H$) to a predictable low concentration ($C_L$), which state is reached when the transient conditions arising at the start of the inert tracer feed to the feedwater have become negligible. For purposes of the present invention, a boiler can be considered operating at a steady state with respect to the inert tracer when there is no significant change in the fluctuation of the inert tracer between $C_H$ and $C_L$ of the concentration of the inert tracer in the boiler and no significant change in the blowdown rate, the feedwater rate, the rate of feeding the tracer to the boiler (or concentration of tracer in the feedwater when introduced therewith) and steaming rate in the absence of boiler leakage. The loss of water due to a leakage can be considered a disruption of the steady state that has been reached. To detect a boiler leakage employing the present process, a steady state as to inert tracer concentration must first be reached, and the $C_L$ and/or $C_H$ values or values proportionate thereto, determined.

Blowdown, as such terminology is understood generally in the boiler field, is water discharged from a boiler system. A sidestream that continuously taps the boiler water for a continuous monitoring of tracer concentration within the boiler would be considered blowdown under this broad definition. Water that leaks from a boiler system would also be considered blowdown under this broad definition. To avoid any confusion of terminology, and to assure that all blowdown streams are precisely defined, the term "normal blowdown" is used herein when water loss from a boiler leak is excluded. At the time of its discharge, the normal blowdown and any other blowdown stream have the same composition(s) as the water retained within the boiler system at that time. The stream of water from a boiler that is monitored for purposes of the present invention may be, for instance, a sidestream off a constantly-flowing normal blowdown stream. Such monitored boiler-water stream also may be a stream from a separate boiler outlet, or a sidestream from the blowdown line ahead of the blowdown valve in a boiler having an intermittent normal blowdown flow. In any of such instances the monitored stream is a part of the "normal blowdown" as defined above, being in all instances intentional and of a generally known rate.

The high concentration $C_H$ of the inert tracer in a boiler for a uniformly cycling boiler system is higher than the average $C_F$ of the normal blowdown, and of course is determined when a boiler-water sidestream is monitored for the concentration of the inert tracer in the boiler. The low concentration $C_L$ of the inert tracer in the boiler is lower than the average $C_F$ of the normal blowdown but, since the boiler water is never entirely replaced with feedwater during cycling, it is never as low as $C_I$.

As mentioned above, the leak-detection function of the present process can be activated only after a steady state as to the inert tracer has been reached. The time required for reaching such steady state after a uniform dosage (feed rate) of inert tracer has begun can be calculated from the following Formula II:

Formula II $t = -(M/B)ln(1 - C_T/C_F)$ wherein M is the mass of the boiler water (in lbs), B is the normal blowdown rate (in lbs/hour), $C_F$ is the concentration or average concentration of the inert tracer in the normal blowdown after steady state is reached, and $C_T$ is the concentration of the inert tracer in the normal blowdown at time t. The M/B factor is a constant (boiler constant "K") for a given boiler operating under a uniform normal blowdown rate. M can be determined from design documents or by spiking the boiler quickly with a known amount of an inert tracer and measuring the value $C_F$ obtained with the normal blowdown shut off. If the mass of the boiler water is unable to be known precisely, a determination that a steady state as to the inert tracer has been reached is made when a uniform average cycles value is seen by monitoring the inert tracer for a period of about one to two weeks while holding $C_I$ constant.

The inert tracer selection for the purposes of the present invention must consider the temperature constraints existing on the waterside of a boiler. The inert tracer preferably is a fluorescence tracer, as discussed below.

Determination of Boiler Cycles and Leakage

In FIG. 1 there is shown in diagrammatical form a boiler system designated by the general reference numeral 10, comprised of a boiler 12, a feedwater line 14 through which feedwater "FW" flows into the boiler 12, a steam line 16 through which the steam generated leaves the boiler 12, and a blowdown line 18 through which normal blowdown "BD" is discharged from the boiler 12. The delivery of feedwater to the boiler 12 is controlled by a feedwater valve 20. The discharge of normal blowdown from the boiler 12 is controlled by a blowdown valve 22. A sidestream 28 off the blowdown line 18 supplies a small continuously cooled sample stream for monitoring the concentration of the inert tracer in the boiler by means of appropriate instrumentation 30, which is shown diagrammatically in FIG. 1, and is discussed in more detail below. A feedwater sidestream 32 is tapped off of the feedwater line 14 and along such feedwater sidestream 32 is a feedwater-monitoring instrumentation 34, discussed below. The rate at which normal blowdown is discharged from the boiler 12 is dictated by the balance desired between the rate of introduction of impurities ("solids") to the boiler 12 together with feedwater and the rate of solids discharge from the boiler 12 with normal blowdown. The desired balance is normally an equal balance. The solids discharge rate should equal the solids introduction rate over a given time period. The concentration of solids within the boiler 12 at any given time, after steady state is reached, should also fall within predetermined limits.

This balance between the rate of introduction of impurities ("solids") to a boiler together with feedwater and the rate of solids discharge from the boiler with normal blowdown may be represented by a hypothetical boiler operation example as follows:

(1) The maximum solids concentration within the boiler at any given time is set for an equivalent of 1,000 mg solids per liter of boiler water;

(2) The feedwater has an average solids concentration of 100 mg/liter, is fed to the boiler at a rate of 1,000,000 lb/day and thus 100 lb of solids are fed to the boiler per day;

(3) The average solids concentration in the normal blowdown is equal to the 1,000 mg/liter solids concentration maximum (see 1 above), 100 lb of solids must be discharged per day (see 2 above) and thus the normal blowdown rate must be 100,000/lb per day; and (4) Steam having an essentially zero solids content is generated and discharged from the boiler at a rate of 900,000 lb per day.

The desired cycles value for such a boiler balance is 1,000/100 = 10. That is, the concentration of solids in the normal blowdown should be 10 times the concentration of solids in the feedwater. However, the typical feedwater solid concentration, due to the pretreatment system operation and the quantities of returned condensate, will have between a 5% and 25% variance range. The more pure the feedwater, the greater the variance range and thus the more difficult it becomes to make accurate boiler cycle measurements from normal feedwater impurities. The actual cycles value is more easily measured by continuously adding a uniform dosage of an inert tracer to the feed water and monitoring its concentration in both the feedwater and normal blowdown, along the feedwater line and blowdown line respectively, and substituting the concentrations determined into Formula I. (It is desirable but not required that the inert tracer be monitored along the feedwater line for the present invention.) If the cycles value determined by the inert tracer was lower than desired, the blowdown rate could be lowered, and if the cycles value determined by the inert tracer was higher than desired, the normal blowdown rate could be increased.

When the blowdown rate is set to provide the desired cycles value, the sidestream 28 off the blowdown line 18 (which need only comprise a negligible fraction of the boiler water) is monitored to determine on a continuous basis the concentration of the inert tracer in the boiler water. The sidestream 28 is ahead of the blowdown valve 22. The concentration of inert tracer monitored by the instrumentation 30 will normally fluctuate from the $C_L$ low value, at the point within the time period after the feedwater rate exceeds the normal blowdown rate, to the high value $C_H$ at a point within the time period before the normal blowdown rate exceeds the feedwater rate. The instrumentation would include one or more setpoints. A low setpoint, for instance, would be below the normal $C_L$ value, and the reaching of such set point would be a variance indicator. A high setpoint would be at about $C_H$, and a failure to reach such setpoint would be a variance indicator. For instance, if the inert tracer concentration in the feedwater of a boiler having a cycles value of 50 is 1 ppm, its average concentration in normal blowdown (average $C_F$) would be 50 ppm. Its high value in the boiler $C_H$ may be about 55 ppm, and its low value $C_L$ would be for instance about 45 ppm. If the tracer concentration in the boiler fell to 40 ppm, there would be a 20 percent difference between this reading and the average $C_F$ reading of 50 ppm, and about an 11 percent difference between this reading and the normal low inert tracer reading $C_L$. There may also be a change in the feedwater rate if the boiler is a constant steam load boiler. This feedwater rate change would be extremely difficult to detect with any assurance using a normal analyzer having an accuracy of about ±3% because the feedwater rate change would be on the order of only about 0.5%. (In a constant steam load boiler, the feedwater rate is the steam rate plus the blowdown rate, and the steam rate for a boiler having a cycles value of about 50 would be about 200 times the normal blowdown rate. Flow meters are generally not used to determine normal blowdown flow rates because of fouling and accuracy problems.)

As noted above, a drop in the $C_L$ value from the normal level or failure to reach the normal $C_H$ while at steady state steaming rate is indicative of a leak. Water has left the boiler by a route other than the generated steam and the normal blowdown discharge, and a proportional amount of inert tracer has left the boiler with that water. The feedwater control system has replaced that lost water with water containing a lesser concentration of the inert tracer, diluting the overall tracer concentration in the boiler water. Such a leakage would cause a water loss that is minute compared to the water content of the boiler, and yet with an inert tracer that is not affected by the feedwater purification efficiency, or other variable parameters of the feedwater, such a water loss and concomitant inert tracer dilution is detectable. For example, as described above, a leakage that causes only a 0.5% increase in water consumption by the boiler would also provide a 20% decrease in the tracer concentration from its average of 50 ppm and an 11% decrease in the tracer concentration from its normal low value of 45 ppm. The amount of the water loss and the precise dilution of the inert tracer need not be quantitatively determined, although such quantitative determinations can be easily made using the method of the present invention. The fact that it is occurring alone will be an invaluable leak-alert benefit to a boiler operator.

Instrumentation

Figure 2:
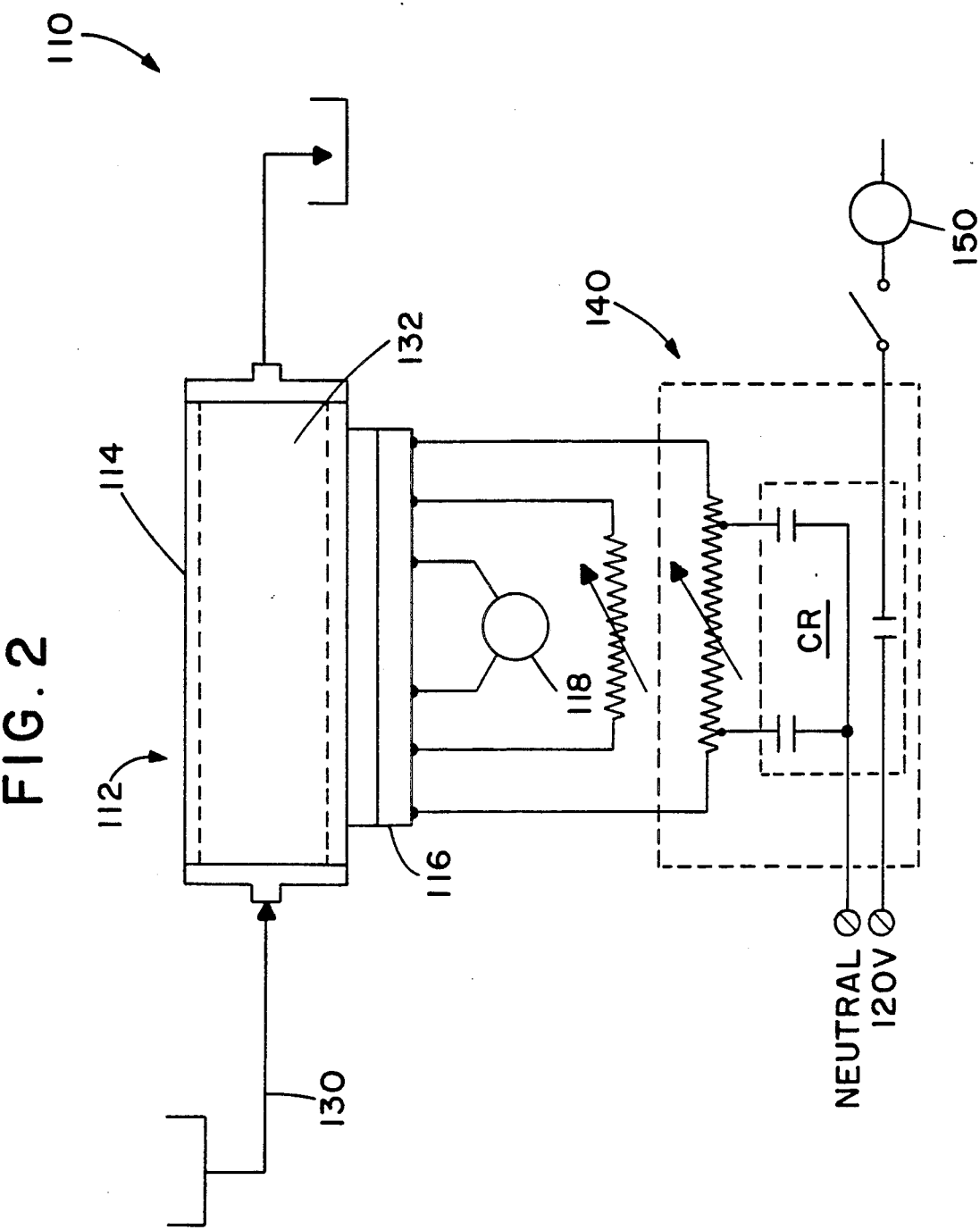
FIG. 2 is instrumentation for continuously monitoring an inert tracer in the boiler and feedwater of a boiler shown schematically.

The preferred instrumentation for continuously monitoring an inert tracer in the boiler is shown schematically in FIG. 2 and designated by the general reference numeral 110. It contains several major components:

1. A sensor or detector 112 for determining from an on-stream characteristic of the inert tracer its concentration in the sample, including an analyzer 114 for measuring the characteristic and a transducer 116 (a power-transforming device inserted between parts of communication systems) that generates an electrical signal (voltage) corresponding to the concentration analysis;

2. An LED digital readout and electronic data recorder device 118 or other register that generates a continuous record of the concentration of the inert tracer in the boiler as a function of time;

3. A leak-alert signal 150 that is activated when the on-stream analysis of the inert tracer fails to reach the predetermined high concentration ($C_H$) in the predetermined normal cycle time period or ever falls below a predetermined low concentration ($C_L$); and 4. A feedback controller (monitor) 140 that allows the signal 150 to be activated depending on the on-stream analysis of the concentration of inert tracer represented by the voltage signal from the transducer 116. After addition of the known concentration $C_I$ to the feedwater, a sample is taken from a convenient blowdown tap location and is passed through a sampling line (conduit) 130 (such as along blowdown sidestream 28 of FIG. 1) into a flow cell 132 of an analyzer 114 where the concentration of the inert tracer in the boiler sample is analyzed continuously. The concentration of the inert tracer is measured on a real-time basis by this analysis of the inert tracer concentration. Cycles at a steady state are monitored and calculated first before the high concentration $C_H$, the low concentration $C_L$ and the normal cycle time period are determined and set for the leak-alert signal 150 that is activated when the on-stream analysis of the inert tracer fails to reach the high-concentration $C_H$ within the normal cycle time period or ever falls to a predetermined concentration of $C_{L-D}$, which is a value less than $C_L$. In addition, the percent holding time may be calculated if desired.

The analyzer 114 is preferably a Turner Designs (Sunnyvale, Calif.) Model Fluorometer 10 AU which has a flow-pressure rating of 70 psi. This fluorometer has a 0.3-centimeter diameter and a two-inch long flowcell 132, which allows for a large fluorescence intensity, the fluorescence intensity from a given source being proportional to cell path. In general, any fluorometer, with a large pathlength, and excitation and detection in the ultraviolet (UV) region can be used.

The flowcell 132 is a quartz cylinder having the dimensions noted above. The flowcell 132 is transparent to ultraviolet radiation emitted by a light source directed against one side of the flowcell 132. At a 90° angle from the light source is the transducer 116 which transforms the emissivity of the fluorescent inert tracer into a 0 to 5 volt DC voltage, emissivity (and therefore voltage output) varying with the concentration of the inert tracer. An LED indicator 118 is responsive to the output voltage of the transducer 116 (0 to 5 volts, DC) enabling the concentration of the inert tracer to be observed. The output recording device 118, for a real-time printout of inert tracer concentration, is responding on a continuous line basis to the voltage output (output of 4 to 20 milliamps) of the transducer 116 element included in the analyzer 114. A monitor 140 having HI, LO relay contacts is in communication with the output of the transducer 116 which in effect evaluates the concentration of inert tracer. If the evaluation does not reach the high concentration standard set for the inert tracer ($C_H$), or the inert tracer concentration falls below the normal level ($C_L$) there is a variance indicator which is indicative of a potential leak and the signal 150 is activated. The setpoints (not shown) in the monitor 140 corresponding to these relays may be, for example, 5 milliamps and 15 milliamps, respectively. One coil (not shown) serves all the contacts shown in FIG. 2; when energized at either of the setpoints, all contacts reverse (closing CR). When CR is closed, a 4 to 20 milliamps signal is generated which is transmitted via a 10 to 20 milliamps signal output to the boiler operator's signal panel signal 150 (or bus or distribution control system, not shown). The continuous monitor 140 as shown in FIG. 2 is employed to monitor the concentration of inert tracer in the boiler. A similar monitor can be set to monitor the feedwater to determine the concentration of the tracer. Monitor readouts for both feedwater and blowdown samples may be ratioed to determine the cycles value when the steady state is reached. Percent life holding time may be calculated.

Figure 3:
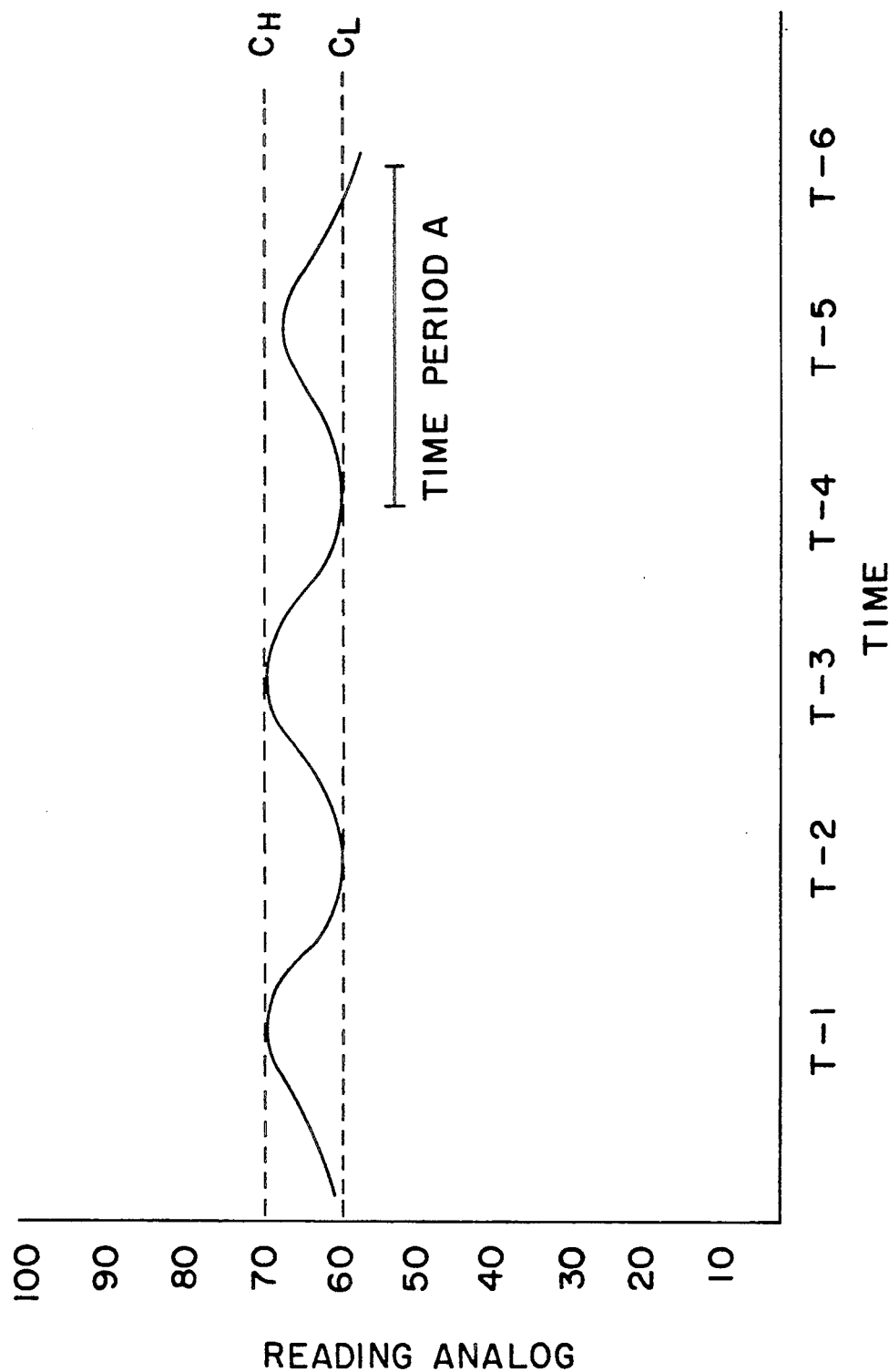
FIG. 3 is a graphical hypothetical performance record involving continuous monitoring and cycles of a boiler.

A hypothetical performance record involving continuous monitoring and cycles is graphically depicted in FIG. 3. Two laboratory calibrations would be checked using two standards, for instance, 0.5 and 0.6 ppm 2-naphthalene sulfonic acid (2-NSA) tracer. The instrument would then be calibrated first against distilled water (DI) at a process simulation site and then against a 0.6 ppm 2-NSA tracer standard. After such a calibration exercise, the instrument would then be used to continuously monitor a boiler receiving feedwater dosed with 0.05 ppm 2-NSA tracer, after a steady state as to the inert tracer was achieved in the boiler. The cyclic rise and fall of the inert tracer concentration in the boiler with time is shown in FIG. 3, and at time T-5 there is shown a deviation from the normal cyclic concentration change, wherein a low tracer concentration condition is reached, indicating that a leakage in this hypothetical boiler system may have started.

Figure 4:
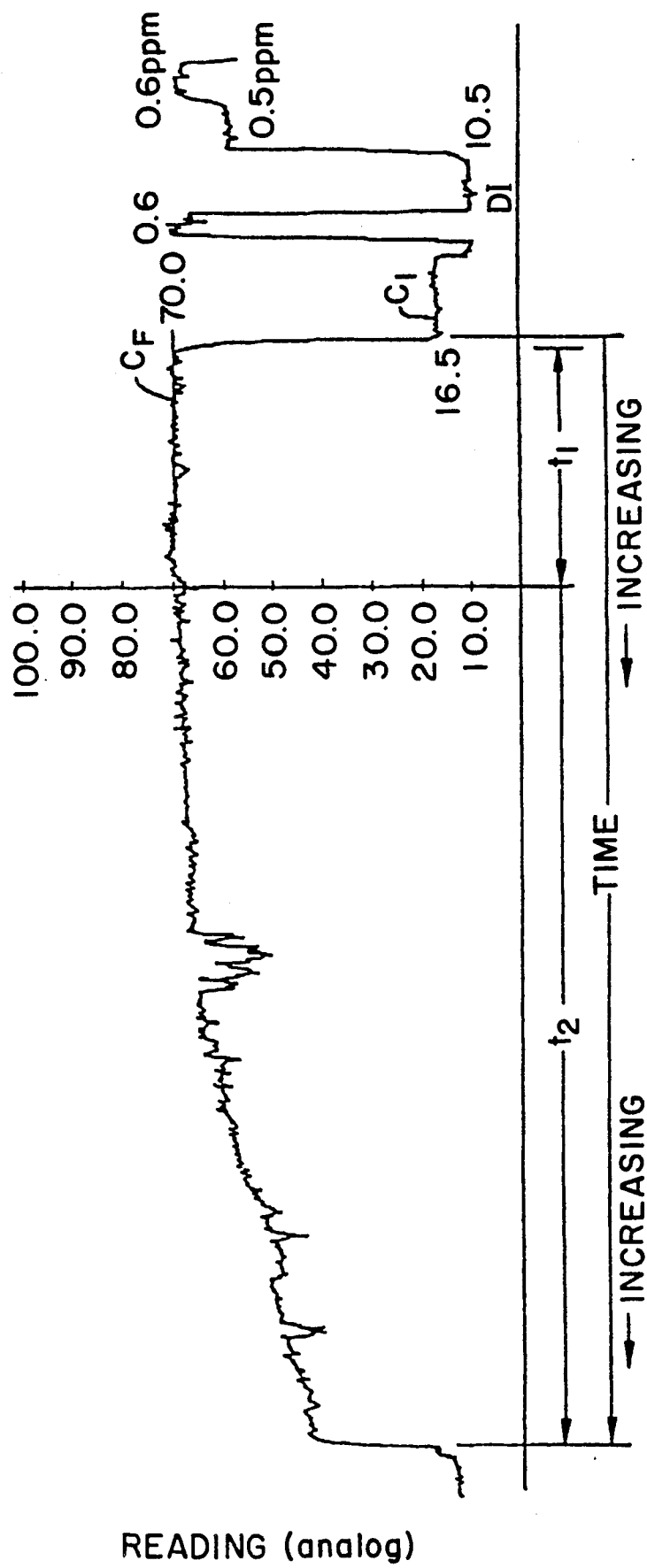
FIG. 4 is a graphical hypothetical continuous register printout for verifying whether the cycles value of a boiler is proper.

From a continuous register printout such as that shown in FIG. 4 it is a simple matter to determine or verify if the cycles are proper. Thus, the background or "control" condition (no tracer) is known (background reading of 10.5), the starting concentration of tracer in the feedwater is known (6.5), and also the normal blowdown concentration at steady state (70). The cycles value is therefore $C_I/C_F = (70 - 10.5)/6.5 = 10.2$.

The invention may be employed concomitantly with the determination of other boiler operational parameters. Thus it will be seen that a continuous recording of the tracer concentration, as a stable component, permits accurate determination of enough $C_I/C_F$ points during the concentration period to plot the straight line of various values of ln $(1 - C_I/C_F)$ in Formula II or to determine the slope which gives the inverse or reciprocal of the boiler constant K. Knowing K, and knowing $C_F$, the unknowns in the holding time equation of $$\%HT(P) = -K\ln[1 - (P/100)]$$

wherein (P) symbolizes percent life of component C and $P = C_P/C_F \times 100$, wherein $C_P$ = the concentration of a component C at the desired %HT, and where $C_F$ = steady state boiler concentration of component C, permits the holding time to be calculated.

Inert Tracers

The inert tracer must be transportable with the water of the boiler system (except of course the water discharged from the boiler as steam) and thus wholly water-soluble therein at the concentration it is used, under the temperature and pressure conditions to be encountered. Preferably the selected inert tracer also meets the following criteria:

1. Be thermally stable and not decompose at the temperature within a boiler;
2. Be detectable on a continuous or semicontinuous basis and susceptible to concentration measurements that are accurate, repeatable and capable of being performed on feedwater and blowdown water;
3. Be substantially foreign to the chemical species that are normally present in the water of the boiler systems in which the inert tracer may be used;
4. Be substantially impervious to interference from, or biasing by, the chemical species that are normally present in the water of the boiler systems in which the inert tracer may be used;
5. Be substantially impervious to any of its own potential specific losses from the water of the boiler system, including selective carry-over;
6. Be compatible with all treatment agents employed in the water of the boiler systems in which the inert tracer may be used, and thus in no way reduce the efficacy thereof;
7. Be compatible with all components of its formulation and such compatibility preferably should endure despite the required concentrations of the tracer and/or other components in such a formulation, and despite the storage and/or transportation conditions encountered; and
8. Be reasonably nontoxic and environmentally safe, not only within the environs of the water of the boiler system in which it may be used, but also upon discharge therefrom.

Generally it is desirable to employ the least amount of inert tracer that is practical for the circumstance, and the amount of the inert tracer added to the water of the boiler system should be at least an amount effective for the determinations desired. Seldom would an inert tracer be deliberately fed to the water of a boiler system in an amount grossly in excess of the minimum effective amount because there generally would be no practical purpose in doing so that would justify the costs involved and any deleterious effects on the quality of the water of the boiler caused by the presence of the inert tracer therein. The amount of inert tracer to be added to the water of the boiler system that is effective without being grossly excessive will vary with a variety of factors including, without limitation, the inert tracer and monitoring method selected, the potential for background interference with the selected monitoring method, the magnitude of the expected inert tracer concentration in the blowdown, the monitoring mode (which generally would be an on-line continuous monitoring mode), and other similar factors. Generally the dosage of an inert tracer to a water of the boiler system will be at least sufficient to provide a concentration of tracer in the blowdown at steady state of at least about 0.1 ppb, and more commonly at least about 5 ppb or higher, up to about 100 or 200 ppm, in the blowdown.

By the terms "tracing" is meant herein, unless expressly indicated otherwise, the determination of the concentration of the inert tracer(s) in the blowdown. Such tracing would seldom be conducted on a singular, intermittent or semi-continuous basis for the purpose of the present invention, but instead on a substantially continuous basis, and preferably the concentration determination is conducted on-site (at the site of the boiler system) to provide a rapid detection of at least the fact that the inert tracer concentration in the boiler or blowdown has dropped from the normal concentration or that the blowdown flow rate has decreased compared to normal. The inert tracer is at times referred to herein merely as a "tracer".

As noted above, the inert tracer must be added to the water of the boiler system in known proportion to the feedwater, and preferably the inert tracer is introduced into the boiler system together with the feedwater at a known and constant concentration therein. The tracer formulation, or "product", may be an aqueous solution or other substantially homogeneous admixture that disperses with reasonable rapidity in the system to which it is added. Since in most any instance an inert tracer would be added to a boiler system as a component of a formulation, rather than as dry solid or neat liquid, the tracer concentration may be correlated not to the numerical concentration of the inert tracer itself but instead to the concentration of a product, which in turn can be correlated to the concentration of the inert tracer when and if such information is required.

In preferred embodiment, the chemical compound(s) selected as an inert tracer(s) should not be one that is consumed or lost to the water of the boiler system, for instance due to degradation, deposition, complexation, or other phenomena, unless such consumption or loss is at a rate that is predictable. The inert tracer(s) used in the present invention is preferably substantially unconsumed in the use environment. An inert tracer(s) that is wholly inert in the water-system environment would not react with any of the components in the water of the boiler system to which it is added, would not degrade in the environment of the water of the boiler system, would be incapable of coupling and/or depositing in any manner within such boiler system and would not appreciably be effected by other system parameters such as metallurgical composition, heat changes or heat content. There are water-soluble inert tracer(s) that are wholly inert, or substantially inert, in the aqueous environments likely to be encountered in industrial boiler systems. Further, it is believed that an inert tracer(s) having a degree of inertness such that no more than 10 weight percent thereof is lost due to reaction, degradation, coupling and/or deposition during the time that elapses between its addition and its discharge as a blowdown component is sufficiently, or substantially, inert for the purpose of the present invention for most, if not all, tracer monitorings.

Among these substantially boiler-system-inert fluorescent compounds are the mono-, di-and trisulfonated naphthalenes, including their water-soluble salts, particularly the various naphthalene mono- and disulfonic acid isomers, which are a preferred inert tracer(s) for use in the present invention. The naphthalene mono- and disulfonic acid isomers are water-soluble, generally available commercially and easily detectable and quantifiable by known fluorescence analysis techniques. Preferred naphthalene mono- and disulfonic acid isomers are the water-soluble salts of naphthalene sulfonic acid ("NSA"), such as 2-NSA, and naphthalene disulfonic acid ("NDSA" or "NDA"), for instance 1,5-NDSA. Many of these inert tracer(s) (mono-, di- and trisulfonated naphthalenes and mixtures thereof) are extremely compatible with the environments of most boiler systems. Among these preferred fluorescent tracers, 2-NSA and (1,5-NDSA) have been found to be thermally stable (substantially inert) at temperatures up to at least about 540° C. (1004° F.), for at least 24 hours at 285° C. (545° F.) and at pressures up to about 1,500 psig for time periods commensurate with commercial boiler holding times. Such inert fluorescent tracers have been found to carryover into the steam discharged from commercial boilers at concentrations of less than 500 ppt when present in the boiler waters at concentrations within the range of from about 5 to 50 ppb, and thus these tracers are not selectively carried over into the steam, and do not carry over into the steam in any appreciable amount. In addition, it has been found that the contribution to conductivity of the mono-, di- and trisulfonated naphthalenes is minimal at the ppb levels used for fluorescence determination in either the boiler feedwater or the blowdown.

Another group of inert fluorescent tracers that are preferred for use in the process of the present invention, particularly under pressures of no more than about 1,000 psi, are the various sulfonated derivatives of pyrene, such as 1,3,6,8-pyrene tetrasulfonic acid, and the various water-soluble salts of such sulfonated pyrene derivatives.

The tracer is preferably selected from among those that are easily quantifiable by a fluorescence analysis method, a preferred analytical technique for the purposes of the present process. Other analysis methods not excluded for use in quantifying the inert tracer are HPLC and fluorescence analysis combinations, which are described in more detail below.

Fluorescence Emission Spectroscopy

The detection and quantification of specific substances by fluorescence emission spectroscopy is founded upon the proportionality between the amount of emitted light and the amount of a fluoresced substance present. When energy in the form of light, including ultra violet and visible light, is directed into a sample cell, fluorescent substances therein will absorb the energy and then emit that energy as light having a longer wavelength than the absorbed light. A fluorescing molecule absorbs a photon resulting in the promotion of an electron from the ground energy state to an excited state. When the electron's excited state relaxes from a higher energy vibrationally-excited state to the lowest energy vibrationally-excited state, energy is lost in the form of heat. When the electron relaxes to the ground electronic state, light is emitted at a lower energy than that absorbed due to the heat-energy loss, and hence at a longer wavelength than the absorption. The amount of emitted light is determined by a photodetector. In practice, the light is directed into the sample cell through an optical light filter so that the light transmitted is of a known wavelength, which is referred to as the excitation wavelength and generally reported in nanometers ("nm"). The emitted light is similarly screened through a filter so that the amount of emitted light is measured at a known wavelength or a spectrum of wavelengths, which is referred to as the emission wavelength and generally also reported in nanometers. When the measurement of specific substances or categories of substances at low concentrations is desired or required, such as often is the case for the process of the present invention, the filters are set for a specific combination of excitation and emission wavelengths, selected for substantially optimum low-level measurements.

In general, the concentration of an inert tracer can be determined from a comparison of a sample's emissions intensity to a calibration curve of the given tracer's concentration versus emissions, for the same set of excitation wavelength/emission wavelengths. Such a concentration-by-comparison method by which the sensed emissions are converted to a concentration equivalent preferably is employed to determine concentration of an inert tracer that are within the concentration range over which a linear emission response is observed, and this concentration range is referred to herein as the "linear-emission-response concentration range". The linear-emission-response concentration range is to some extent dependent upon the specific inert tracer and the excitation wavelength/emission wavelength set employed. At inert tracer concentrations higher than a given inert tracer's linear-emission-response concentration range, there is a negative deviation from ideal (linear) behavior, the degree of emission for a given concentration being less than predicted by a linear extrapolation. In such instances, the sample can be diluted by known factors until the concentration of the inert tracer therein falls within the linear-emission-response concentration range. If the inert tracer is present in the sample at only very low concentrations, there are techniques for concentrating the inert tracer by known factors until its concentration falls within the linear-emission-response concentration range or is otherwise more readilt measured, for instance by liquid-liquid extraction. Nonetheless, preferably a calibration curve over the linear-emission-response concentration range would be prepared or obtained before employing a given inert tracer, and preferably the inert tracer would be added to the feedwater of the boiler system in an amount sufficient to provide a concentration of the inert tracer in the boiler that is within the linear-emission-response concentration range. Generally the linear-emission-response concentration range of an inert tracer is sufficiently broad to readily estimate the amount of the inert tracer that will be sufficient for this purpose. A linear-emission-response concentration range will most often extend through a concentration range from a concentration of "m" to a concentration of at least 10 m.

A determination of the presence of a fluorescent inert tracer and preferably the concentration thereof in the blowdown from a boiler system can be made when the concentration of the inert tracer in the boiler is only several parts per million (ppm) or even parts per billion (ppb) for some of the inert tracer that can be employed in the process of the present invention. In preferred embodiment, the amount of a fluorescent inert tracer added to the boiler system should be sufficient to provide a concentration of the inert tracer in the blowdown to be analyzed of from about 5 ppb to about 100 or 200 ppm, although the preferred inert tracers specifically mentioned herein need not be present in the sample analyzed in excess of about 5 or 7 ppm. Such analyses, that is, the measurements of the light emitted in response to the light transmitted to the blowdown, can be made on-site, preferably on an almost instant and continuous basis, with simple portable equipment, such as the photodetector and screens described above.

At times it may be desired to employ a plurality of inert tracers. For instance, it may be desired to use a plurality of inert tracers to confirm that neither is undergoing any tracer-specific loss or one tracer to detect a given variance and another for the detection of a different variance or other parameter. Such separate and distinct inert tracers can each be detected and quantified in a single water blowdown fraction despite both being fluorescent tracers if their respective wavelengths of emission do not interfere with one another. Thus concurrent analyses for multiple inert tracers is possible by selection of inert tracers having appropriate spectral characteristics. Preferably widely separated wavelengths of radiation should be used to excite each of the inert tracers and their fluorescent emissions should be observed and measured at widely separated emission wavelengths. A separate concentration calibration curve may be prepared or obtained for each inert tracer. In other words, more than one inert tracer can be employed, and then the presence and/or concentration of each such inert tracer in the boiler system should be determined using analytical parameters (particularly the excitation/emission wavelengths) effective for each such inert tracer, which analytical parameters preferably are sufficiently distinct to differentiate between measurements.

Fluorescence emission spectroscopy on a substantially continuous basis, at least over a given time period, is one of the preferred analytical techniques for the process of the present invention. It is one of the preferred analysis techniques for quantifying and determining the concentration of the inert tracer in a boiler system and it is an analysis technique having significant advantages. Fluorescent chemical tracers and monitoring techniques are now known, for instance as disclosed in U.S. Pat. No. 4,783,314, J. E. Hoots and B. E. Hunt, issued Nov. 8, 1988, incorporated herein by reference, wherein inert fluorescent tracers are employed in combination with a fluorescence monitoring, such as the sodium salt of 2-naphthalenesulfonic acid.

When the inert tracer is 2-NSA, one of the water-soluble salts of napththalene sulfonic acid ("NSA"), its concentration in the blowdown from a boiler system can be fluorometrically measured by excitation at 277 nm and emission measurement at 334 nm, and the emissions observed referenced to a standard aqueous solution containing 0.5 ppm 2-NSA, as acid actives.

A Gilford Fluoro IV dual-monochromator spectrofluorometer can be used for a fluorometric analysis conducted on an intermittent basis and for on-line fluorescence monitoring, a portable fluorometer equipped with appropriate excitation and emission filters and a quartz flow through cell can be used, such as is commercially available from Turner Designs (Sunnyvale, Calif.) Model Fluorometer 10 AU, which is mentioned above.

In general for most fluorescence emission spectroscopy methods having a reasonable degree of practicality, it is preferable to perform the analysis without isolating in any manner the inert tracer. Thus there may be some degree of background fluorescence in the blowdown on which the fluorescence analysis is conducted, which background fluorescence may come from chemical compounds in the boiler system that are unrelated to the present process. In instances where the background fluorescence is low, the relative intensities (measured against a standard fluorescent compound at a standard concentration and assigned a relative intensity for instance 100) of the fluorescence of the tracer versus the background can be very high, for instance a ratio of 100/10 or 500/10 when certain combinations of excitation and emission wavelengths are employed even at low fluorescent compound concentrations, and such ratios would be representative of a "relative fluorescence" (under like conditions) of respectively 10 and 50. In preferred embodiment, the excitation/emission wavelengths and/or the amount of tracer employed are selected to provide a relative fluorescence of at least about 5 or 10 for the given background fluorescence anticipated.

For instance, for most boiler water backgrounds, a compound that has a relative fluorescence of at least about 5 at a reasonable concentration is very suitable as an inert tracer. When there is or may be a specific chemical specie of reasonably high fluorescence in the background, the tracer and/or the excitation and/or emission wavelengths often can be selected to nullify or at least minimize any interference of the tracer measurement(s) caused by the presence of such specie.

One method for the continuous on-stream monitoring of chemical tracers such as the inert tracer by fluorescence emission spectroscopy and other analysis methods is described in U.S. Pat. No. 4,992,380, B. E. Moriarity, J. J. Hickey, W. H. Hoy, J. E. Hoots and D. A. Johnson, issued Feb. 12, 1991, incorporated hereinto by reference.

Combined HPLC-Fluorescence Analysis

The combination of high-pressure liquid chromatography ("HPLC") and fluorescence analyses of fluorescent tracers is a powerful tool for the present process, particularly when very low levels of the inert tracer are used or the background fluorescence encountered would otherwise interfere with the efficacy of the fluorescence analysis. The HPLC-fluorescence analysis method allows the tracer compound to be separated from the fluid matrix and then the tracer concentration can be measured. The combination of HPLC-fluorescence analysis is particularly effective for measuring minute levels of tracer in highly contaminated fluids.

The HPLC method can also be effectively employed to separate a tracer compound from a fluid matrix for the purposes of then employing a tracer-detection method other than the fluorescence analysis, and such other tracer-detection methods include without limitation light absorbance, post-column derivatization, conductivity and the like, which methods are described in "Techniques in Liquid Chromatography", C. F. Simpson ed., John Wiley & Sons, New York, pp 121-122, 1982, incorporated hereinto by reference, and "Standard Method For The Examination Of Water And Wastewater", 17th Edition, American Public Health Association, pp 6-9 to 6-10, 1989, incorporated hereinto by reference.

Analytical techniques for quantifying the presence and/or concentration of a chemical specie without isolation thereof are within an evolving technology, and the above survey of reasonable analytical techniques for use in monitoring the inert tracer in the process of the present invention may presently not even be exhaustive, and most likely techniques equivalent to the above for the purposes of the present invention will be developed in the future.

An inert tracer may be selected for a given process based on a preference for one or more analytical techniques, or an analytical technique may be selected for a given process based on a preference for one or more inert tracers.

As noted above, in preferred embodiment, the chemical compound(s) selected as the inert tracer should be soluble in the boiler system to which it is added and should be either stable in the environment thereof for the useful life expected of the inert tracer, or its loss from the fluid due to degradation, deposition, complexation, or other phenomena should be predictable and compensative, particularly since it is desired not merely to detect the presence of some amount of the inert tracer, but also to determine the concentration thereof, or change in concentration. In preferred embodiment, the combination of the chemical compound(s) selected as the inert tracer and the analytical technique selected for determining the presence of such tracer, should permit such determination without isolation of the inert tracer, and more preferably should permit such determination on a continuous and/or on-line basis.

The present invention is a method of determining leakage from a boiler water system wherein steam is generated in a boiler from feedwater fed to the boiler, the feedwater introducing impurities to the boiler water and the concentration of the impurities in the boiler water within the boiler is reduced by withdrawing fractions thereof as blowdown while admitting additional feedwater as boiler-water makeup. The boiler would have a concentration cycle value, the concentration cycle value being the average value of the concentration of an inert component in the blowdown at steady state $C_F$ divided by the concentration of the inert component in the feedwater $C_I$. The concentration of the inert component in the boiler at steady state varies from a high concentration $C_H$, having a value that is higher than $C_F$, to a low concentration $C_L$, having a value between the $C_I$ and $C_F$, within a time period. The method comprises:

employing as the inert component an inert tracer added to the boiler water at a rate equivalent to a known concentration $C_I$ of the inert tracer with respect to the feedwater;

sensing a characteristic of the inert tracer in the boiler at steady state equivalent to its concentration in the boiler water;

converting the sensed characteristic to a value equivalent to the concentration of the inert tracer in the boiler water;

optionally recording the cyclic concentration fluctuation of the inert tracer from $C_H$ to $C_L$ in the boiler water; and activation of a signal upon the detection of an indicator of a variance in the cyclic concentration fluctuation of the inert tracer that is consistent with a leakage of boiler water.

In preferred embodiment the variance indicator is an inert tracer concentration in the boiler that has value less than that equivalent to the normal low $C_L$ concentration of the inert tracer or an inert tracer concentration in the boiler that fails to reach the normal high $C_H$ concentration within a time period B, the time period B being at least about that of the time period in which the fluctuation of the inert tracer between $C_H$ and $C_L$ normally occurs. In preferred embodiment the variance indicator is an inert tracer concentration in the boiler that has value less than that equivalent to the normal low $C_L$ concentration of the inert tracer and wherein the variance indicator is a concentration of the inert tracer of $C_L - C_D$, wherein $C_D$ is at least about 5 percent of the value of $C_L$.

In preferred embodiment the variance indicator is an inert tracer concentration in the boiler that fails to reach the normal high $C_H$ concentration within a time period B and wherein the boiler has open/close blowdown valve operations and the time period B is measured from the closing of the blowdown valve to the time at which the blowdown valve would normally reopen.

In preferred embodiment the boiler system has a normally-open blowdown valve that adjusts the blowdown rate depending upon some indicated component build-up within the boiler, wherein when the inert tracer concentration in the boiler has a value less than that equivalent to the normal low $C_L$ concentration of the inert tracer, the normally-open blowdown valve would close in response to the reading, and wherein the tracer monitoring apparatus is ahead of the blowdown valve and the monitoring apparatus sees a tracer concentration while a flow meter downstream of the blowdown valve sees no flow, and the combination of conditions is the variance indicator.

In another preferred embodiment of the present invention, the boiler system has a normally-open blowdown valve that adjusts the blowdown rate depending upon the concentration of the inert tracer within the boiler. If leakage has started, when the inert tracer concentration in the boiler has a value equivalent to the normal low $C_L$ concentration of the inert tracer, the normally-open blowdown valve would close or there would be no blowdown flow through the normal blowdown line, because the water lost from the boiler due to the leak is a sufficient amount of blowdown to satisfy the $C_L$ concentration condition. The concentration of the inert tracer would eventually fall below the $C_L$ concentration as the water loss from the leak increases. Before the inert tracer concentration falls below its normal $C_L$ concentration, the closing of the normally-open blowdown valve or no blowdown flow through the normal blowdown line in combination with an inert tracer concentration in the boiler equivalent to its normal low $C_L$ concentration is a variance indicating a leakage.

In preferred embodiment the boiler system has a normally-open blowdown valve that adjusts the blowdown rate depending upon some indicated component build-up within the boiler, wherein when the inert tracer concentration in the boiler has a value less than that equivalent to the normal low $C_L$ concentration of the inert tracer the normally-open blowdown valve would close in response to the a reading, and wherein the tracer monitoring apparatus is downstream of the blowdown valve and the apparatus sees no tracer concentration and that condition is the variance indicator.

In other preferred embodiments the variance indicator is an inert tracer concentration in the boiler that has value less than that equivalent to the normal low $C_L$ concentration of the inert tracer or an inert tracer concentration in the boiler that fails to reach the normal high $C_H$ concentration within a time period B, the time period B being at least about that of the time period in which the fluctuation of the inert tracer between $C_H$ and $C_L$ normally occurs, and wherein the variance indicator is an operating parameter of the boiler system and the signal is activated only when the variance indicator is detected at the same time that an imbalance in the operating parameter is seen. For example, the fluctuation of the inert tracer concentration in the boiler water between $C_H$ and $C_L$ is compared to the balance in steam load in the boiler determined from flow signals, and an imbalance between the rate feedwater is flowing into the boiler and the rate steam is being discharged therefrom must be seen by the monitoring apparatus at the same time the variance indicator in the normal fluctuation of the inert tracer concentration indicates a leak before the signal is activated. In another example, the fluctuation of the inert tracer concentration in the boiler water between $C_H$ and $C_L$ is compared to the balance in the holding time of the boiler and a calculated blowdown rate of the boiler, and an imbalance between the holding time and the calculated blowdown rate must be seen by the monitoring apparatus at the same time as a variance indicator in the normal fluctuation of the inert tracer concentration indicates a leak before the signal is activated.

In preferred embodiment the inert tracer is fluorescent, in which the sensed characteristic of the inert tracer is the intensity of the inert tracer's fluorescence emissivity. In more preferred embodiment the selection of the inert tracer, the amount of the inert tracer added to the boiler water and wavelengths of excitation and emission selected for sensing the inert tracer's fluorescence emissivity provide a relative fluorescence of the inert tracer of at least about 5 for the background fluorescence of the boiler water. In another more preferred embodiment the $C_L$ concentration of the inert tracer at the steady state is at least about 1 ppb. In preferred embodiment the $C_L$ concentration of the inert tracer at the steady state is at least about 1 ppb and the $C_H$ concentration of the inert tracer at the steady state is no more than about 200 ppm. The inert tracer is preferably a monosulfonated naphthalene, disulfonated naphthalene, trisulfonated naphthalene, a sulfonated pyrene or water-soluble salt thereof, particularly a water-soluble salt of 2-naphthalene sulfonic acid, 1,5-naphthalene disulfonic acid or 1,3,6,8-pyrene. In another more preferred embodiment the $C_L$ concentration of the inert tracer at the steady state is from about 5 ppb to about 7 ppm.

The inert tracer is preferably introduced into the boiler as a component of the feedwater in the known concentration $C_I$ therein. In more preferred embodiment the average cycles value of $C_F/C_I$ is determined by the average concentrations of the inert tracer in the feedwater and the blowdown and the cycles value is compared to a standard operating cycles value for the operation of the boiler, and in which the blowdown rate may be changed if the determined cycles value is not the standard operating cycles value.

Unless expressly indicated otherwise herein, the inclusion of a prefix or suffix in parenthesis designates the word with such prefix or suffix as an alternative. For instance, "specie(s)" means "specie and/or species", "determination(s)" means "determination and/or determinations", "technique(s)" means "technique and/or techniques", "location(s)" means, "chemical(s)" means "chemical and/or chemicals", "component(s)" means "component and/or components", "tracer(s)" means "tracer and/or tracers", and the like. By "ppm" is meant "parts per million" by weight. By "ppb" us meant "parts per billion" by weight.

The concentration of the inert tracer in the boiler for the purposes of the present invention is determined by the concentration of the inert tracer in a boiler water sample, which generally would be after that sample has been removed from the boiler, and such sample is thus within the broad definition of blowdown regardless of whether or not such sample is derived from the normal blowdown line or not. The terminology of "normal blowdown" excludes water lost from a boiler by leakage but not a water stream monitored for the concentration of the inert tracer whether such stream is part of or separate from the blowdown flow set to remove impurities from the boiler.

Industrial Applicability of the Invention

The present invention is applicable to all industries employing a boiler or boiler system for which an inert tracer is available.

We claim:

1. A method of determining leakage from a boiler water system wherein steam is generated in a boiler from feedwater fed to said boiler, said feedwater introducing impurities to boiler water within said boiler and the concentration of said impurities in said boiler water within said boiler is reduced by withdrawing fractions of said boiler water from said boiler as normal blowdown by means of a blowdown valve operation while admitting additional feedwater to said boiler as boiler-water makeup, said boiler having a concentration cycle value, said concentration cycle value being the average value of the concentration of an inert component in said boiler water at steady state $C_F$ divided by the concentration of said inert component in said feedwater $C_I$, said concentration of said inert component in said boiler at steady state varying from a normal high concentration $C_H$, said normal high concentration $C_H$ having a value higher than said $C_F$, to a normal low concentration $C_L$, said normal low concentration $C_L$ having a value between said $C_I$ and said $C_F$, within a time period, comprising:

employing as said inert component an inert tracer added to said boiler water at a rate equivalent to a known concentration $C_I$ of said inert tracer with respect to said feedwater;

sensing a characteristic of said inert tracer in said normal blowdown at steady state correlated to its concentration in said boiler water on a substantially continuous basis and thereby obtaining a plurality of sensed characteristic values;

converting said plurality of sensed characteristic values to a plurality of values each equivalent to said concentration of said inert tracer in said boiler water;

optionally recording said cyclic concentration fluctuation of said inert tracer from $C_H$ to $C_L$ in said boiler water; and activation of a signal upon the detection of a variance indicator that indicates a variance in said cyclic concentration fluctuation consistent with a leakage of a fraction of said boiler water from said boiler in combination with a posture of said blowdown valve.

2. The method of claim 1 wherein said blowdown valve operation is a normally-open blowdown valve that adjusts the blowdown rate depending upon an indicated component build-up within said boiler, wherein said normally-open blowdown valve closes when said inert tracer concentration in said boiler water is less than said normal low concentration $C_L$ of said inert tracer, wherein a tracer monitoring apparatus is ahead of said blowdown valve, wherein said variance indicator is said monitoring apparatus seeing a tracer concentration while a flow meter downstream of said blowdown valve sees no blowdown discharge flow.

3. The method of claim 1 wherein said blowdown valve operation is a normally-open blowdown valve that adjusts the blowdown rate of flow through a normal blowdown depending upon the concentration of said inert tracer in said boiler water, wherein said variance indicator is an inert tracer concentration in said boiler equivalent to said normal low concentration $C_L$ of said inert tracer when said normally-open blowdown valve is closed or there is a zero rate of said blowdown flow through said normal blowdown line.

4. The method of claim 1 wherein said blowdown valve operation is a normally-open blowdown valve that adjusts the blowdown rate depending upon some indicated component build-up within said boiler, wherein said normally-open blowdown valve would close in response to a reading that said inert tracer concentration in said boiler has a value less than said normal low concentration $C_L$ of said inert tracer, and wherein a tracer monitoring apparatus is downstream of said blowdown valve and said variance indicator is said monitoring apparatus seeing no tracer concentration.

5. The method of claim 1 wherein said inert tracer is a fluorescent tracer having a fluorescence emissivity upon excitation, and wherein said sensed characteristic of said inert tracer is the intensity of said fluorescence emissivity.

6. The method of claim 5 wherein said inert tracer is a water-soluble salt of 2-naphthalene sulfonic acid, or a water-soluble salt of 1,5-naphthalene disulfonic acid, or a water-soluble salt of 1,3,6,8-pyrene tetrasulfonic acid.

7. A method of determining leakage from a boiler water system wherein steam is generated in a boiler from feedwater fed to said boiler, said feedwater introducing impurities to boiler water within said boiler and the concentration of said impurities in said boiler water within said boiler is reduced by withdrawing fractions of said boiler water from said boiler as normal blowdown while admitting additional feedwater as boiler-water makeup, said boiler having a concentration cycle value, said concentration cycle value being the average concentration of an inert component in said boiler water at steady state $C_F$ divided by the concentration of said inert component in said feedwater $C_I$, said concentration of said inert component in said boiler water at steady state varying in a cyclic concentration fluctuation from a normal high concentration $C_H$, said normal high concentration $C_H$ having a value higher than said $C_F$, to a normal low concentration $C_L$, said normal low concentration $C_I$ having a value between said $C_I$ and said $C_F$, within a time period, comprising:

employing as said inert component an inert tracer to said boiler water at a rate equivalent to a known concentration $C_I$ of said inert tracer with respect to said feedwater;

sensing a characteristic of said inert tracer in said normal blowdown at steady state correlated to its concentration in said boiler water on a substantially continuous basis and thereby obtaining a plurality of sensed characteristic values;

converting said plurality of sensed characteristic values to a plurality of values each equivalent to said concentration of said inert tracer in said boiler water and therefrom determining said cyclic concentration fluctuation of said inert tracer;

optionally recording said cyclic concentration fluctuation of said inert tracer;

wherein a variance indicator is an inert tracer concentration in said boiler water less than said normal low $C_L$ concentration of said inert tracer or an inert tracer concentration in said boiler water that fails to reach said normal high $C_H$ concentration within a time period B, said time period B being at least about that of the time period in which said fluctuation of said inert tracer between said normal high concentration $C_H$ and said normal low concentration $C_L$ normally occurs, and comparing said variance indicator to an operating parameter of said boiler system and activating a signal when said variance indicator is detected at the same time than an imbalance in said operating parameter is seen.

8. The method of claim 7 wherein said operating parameter is the balance in steam load in said boiler determined from flow signals, and wherein said imbalance is an imbalance between the rate feedwater is flowing into said boiler and the rate steam is being discharged from said boiler.

9. The method of claim 7 wherein said operating parameter is a balance between the holding time of said boiler and a calculated blowdown rate of said boiler, and wherein said imbalance is an imblance between said holding time and said calculated blowdown rate.

10. A method of determining leakage from a boiler water system wherein steam is generated in a boiler from feedwater fed to said boiler, said feedwater introducing impurities to boiler water within said boiler and the concentration of said impurities in said boiler water within said boiler is reduced by withdrawing fractions of said boiler water from said boiler as normal blowdown while admitting additional feedwater as boiler-water makeup, said boiler having a concentration cycle value, said concentration cycle value being the average concentration of an inert component in said boiler water at steady state $C_F$ divided by the concentration of said inert component in said feedwater $C_I$, said concentration of said inert component in said boiler at steady state varying in a cyclic concentration from a normal high concentration $C_H$, said normal high concentration $C_F$ having a value that is higher than $C_F$, to a normal low concentration $C_L$, said normal low concentration $C_L$ having a value between said $C_I$ and said $C_F$, within a time period, comprising:

employing as said inert component an inert tracer added to said boiler water at a rate equivalent to a known concentration $C_I$ of said inert tracer with respect to said feedwater;

sensing a characteristic of said inert tracer in said normal blowdown at steady state correlated to its concentration in said boiler water on a substantially continuous basis and thereby obtaining a plurality of sensed characteristic values;

converting said plurality of sensed characteristic values to a plurality of values each equivalent to said concentration of said inert tracer in said boiler water and therefrom determining said cyclic concentration fluctuation of said inert tracer from said normal high concentration $C_H$ to said normal low concentration $C_L$ in said boiler water;

optionally recording said cyclic concentration fluctuation of said inert tracer from said normal high concentration $C_H$ to said normal low concentration $C_L$ in said boiler water; and activation of a signal upon the detection of a variance indicator that indicates a variance in said cyclic concentration fluctuation of said inert tracer consistent with a leakage of a fraction of said boiler water from said boiler.

11. The method of claim 10 wherein said variance indicator is an inert tracer concentration in said boiler water that fails to reach said normal high $C_H$ concentration within a time period B, said time period B being at least about that of said time period in which said cyclic fluctuation of said inert tracer between said normal high concentration $C_H$ and said normal low concentration $C_L$ normally occurs.

12. The method of claim 10 wherein said variance indicator is an inert tracer concentration in said boiler water that has value less than said normal low $C_L$ concentration of said inert tracer.

13. The method of claim 10 wherein said variance indicator is an inert tracer concentration in said boiler water that has value less than said normal low $C_L$ concentration of said inert tracer and wherein said variance indicator is a concentration of said inert tracer in said boiler water of $C_L - C_D$, wherein $C_D$ is at least about 5 percent of the value of said normal low concentration $C_L$.

14. The method of claim 10 wherein said variance indicator is an inert tracer concentration in said boiler water that fails to reach said normal high $C_H$ concentration within a time period B and wherein said boiler has a blowdown valve having open/close blowdown valve operations and said time period B is the normal time interval between the closing of said blowdown valve to the time at which said blowdown valve would normally reopen.

15. The method of claim 10 wherein said inert tracer is added to said boiler water as a component of a formulated product.

16. The method of claim 10 wherein said inert tracer is a fluorescent tracer having a fluorescence emissivity upon excitation, and wherein said sensed characteristic of said inert tracer is the intensity of said fluorescence emissivity.

17. The method of claim 16 wherein the chemical specie used as said inert tracer, the amount of said inert tracer added to said boiler water, and wavelengths of excitation and emission used for sensing said fluorescence emissivity provide a relative fluorescence of said inert tracer of at least about 5 for the background fluorescence of said boiler water.

18. The method of claim 16 wherein said normal low concentration $C_L$ of said inert tracer at said steady state is from about 5 ppb to about 7 ppm.

19. The method of claim 16 wherein said inert tracer is a monosulfonated naphthalene, disulfonated naphthalene, trisulfonated naphthalene, a sulfonated pyrene or water-soluble salt thereof.

20. The method of claim 16 wherein said inert tracer is a water-soluble salt of 2-naphthalene sulfonic acid or 1,5-naphthalene disulfonic acid or a water-soluble salt of 1,3,6,8-pyrene tetrasulfonic acid.

21. The method of claim 10 wherein said inert tracer is introduced into said boiler as a component of said feedwater in said known concentration $C_I$ therein.

22. The method of claim 21 further including the steps of determining said concentration cycle value, comparing said concentration cycle value to a standard operating cycles value for the operation of said boiler, and changing the blowdown rate or a dosage of a treating agent if said concentration cycle value is not said standard operating cycles value.

* * * * *